(12) United States Patent
Bratz et al.

(10) Patent No.: US 6,559,098 B1
(45) Date of Patent: May 6, 2003

(54) SULPHONYLUREA AND/ADJUVANT BASED SOLID MIXTURES

(75) Inventors: Matthias Bratz, Limburgerhof (DE); Karl-Friedrich Jäger, Limburgerhof (DE); Rainer Berghaus, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/355,743

(22) PCT Filed: Feb. 4, 1998

(86) PCT No.: PCT/EP98/00413

§ 371 (c)(1), (2), (4) Date: Aug. 4, 1999

(87) PCT Pub. No.: WO98/34482

PCT Pub. Date: Aug. 13, 1998

(30) Foreign Application Priority Data

Feb. 5, 1997 (DE) .......................................... 197 04 276

(51) Int. Cl.⁷ ........................ A01N 43/54; A01N 43/66; A01N 43/40; A01N 43/74
(52) U.S. Cl. ........................ 504/116; 504/133; 504/134; 504/136; 504/212; 504/214; 504/321; 504/332; 504/211
(58) Field of Search .................................. 504/133, 134, 504/136, 116, 212, 214, 321, 332

(56) References Cited

U.S. PATENT DOCUMENTS

| | | | |
|---|---|---|---|
| 4,511,395 A | * 4/1985 | Misselbrook | 71/121 |
| 4,933,000 A | 6/1990 | Somlo | 71/93 |
| 5,543,385 A | 8/1996 | Roechling et al. | 504/127 |
| 5,612,046 A | * 3/1997 | Chin et al. | 424/405 |
| 5,650,375 A | * 7/1997 | Hacker et al. | 504/136 |
| 5,928,997 A | 7/1999 | Bauer et al. | 504/133 |

FOREIGN PATENT DOCUMENTS

| | | |
|---|---|---|
| EP | 313317 | 4/1989 |
| EP | 367887 | 5/1990 |
| EP | 378895 | 7/1990 |
| EP | 413267 | 2/1991 |
| EP | 554015 | 8/1993 |
| EP | 764404 | 3/1997 |
| JP | 62084004 | 4/1987 |
| JP | 5271021 | 10/1993 |
| WO | 90/00007 | 1/1990 |
| WO | 91/04666 | 4/1991 |
| WO | 92/12637 | 8/1992 |

OTHER PUBLICATIONS

Guo et al. (DN 131:347860, CAPLUS, abstract of CN 1154795).*
Nalewaja et al., Weed Tech., 9(4), 1995, 689–695.
Dunne et al., Weed Sci., (1994), vol. 42, 82–85.
Green et al., Weed Tech., 7(3), 1993, 633–640.

* cited by examiner

Primary Examiner—Sabiha Qazi
(74) Attorney, Agent, or Firm—Keil & Weinkauf

(57) ABSTRACT

Solid mixtures comprising
a) an active ingredient from the group of the sulfonylureas and
b) a sulfate- or sulfonate-containing surfactant.

7 Claims, No Drawings

SULPHONYLUREA AND/ADJUVANT BASED SOLID MIXTURES

This application is a 371 of PCT/EP98/00413 filed on Feb. 4, 1998.

The present invention relates to solid mixtures based on sulfonylureas and adjuvants.

Sulfonylureas (termed "SU" hereinafter) are a group of highly active herbicides which are used widely in crop protection.

Due to the mechanism of active ingredient uptake via the leaf, it is possible to improve the activity of SU by adding surface-active substances such as wetters to the spray mixture (cf. Green et al.,ANPP, Seizieme conference du columa—Journees internationales sur la lutte contre les mauvaises herbes 1995, pp. 469–474; "DPX-KG 691—A new surfactant for sulfonylurea herbicides").

Substances which are described in the literature as being particularly suitable wetters are, inter alia, oil adjuvants (Nalejewa et al., Weed Technol. 1995, 9, pp. 689–695) or alcohol ethoxylates (see above and Dunne et al., Weed Science 1994, 42, pp. 82–85; Green, Weed Technol. 1993, 7, pp. 633–640). In agricultural practice, these substances are added to the spray mixture by the practitioner in the form of tank mix additives. The mixture of SU herbicide and surfactant is prepared in the spray tank a short time prior to use.

An example of a commercially available product is a twin pack with the trade name CATO® (Du Pont de Nemours), which is composed of water-dipersible granules in which the active ingredient rimsulfuron (component A) amounts to 25%, and of a wetter (component B) packaged separately and composed of a mixture of 2-butoxyethanol, polyethoxylated tallow amine and nonylphenyl polyethylene glycol ether. For use, the two components are mixed in the spray tank as described above.

Under practice conditions, it would be desirable to be able to employ finished formulations which already comprise an activity-enhancing wetter, so as to avoid mixing immediately prior to use, which is problematic. This would allow logistics problems and mixing errors to be avoided when making the spray mixture. Moreover, solid formulations are generally advantageous, from the point of view of application, as far as designing and disposing of the packaging is concerned.

The literature furthermore discloses that formulations which comprise sulfonlyureas are problematic with regard to active ingredient stability, since the active ingredient may undergo decomposition in the course of time when the conditions are unfavorable. If this happens, the desired herbicidal activity is lost. The tendency to decomposition is also a problem with regard to the registration requirements, since the stability of PS-type active ingredients in formulations must meet certain minimum requirements upon registration.

JP-A 62/084004 describes the use of calcium carbonate and sodium tripolyphosphate for stabilizing SU-containing formulations.

JP-A 63/023806 describes how this problem can be solved by using specific carriers and vegetable oils for the preparation of solid SU-containing formulations. JP-A 08/104603 describes similar effects when using epoxidized natural oils. The two applications mentioned above share the feature of incorporating vegetable oils into the solid formulation in order to exploit not only an improved stability, but also the activity-enhancing effects of these substances, which act as adjuvants.

Similar effects are exploited, (cf. EP-A 313317 and EP-A 554015) when incorporating vegetable oils into liquid formulations (as a rule, suspension concentrates).

It is also known from the prior art to use sulfate- or sulfonate-containing surfactants as wetters/adjuvants.

EP-A 378 895 and WO92/12637 describe sulfate- or sulfonate-containing surfactants together with the active ingredient N-phosphonomethylglycine in solid formulations.

EP-A 413 267 describes the use of sulfate- or sulfonate-containing surfactants together with the active ingredients glufosinate-ammonium and fenoxaprop-ethyl.

It is an object of the present invention to provide solid formulations with sulfonylureas as active ingredients which comprise adjuvants in the solid formulation itself and which are superior to prior-art solid formulations.

We have found that this object is achieved by solid mixtures which comprise a) a sulfonylurea and b) an adjuvant from the group of the sulfate- or sulfonate-containing surfactants.

Surprisingly, it has been found that the use of sulfate- or sulfonate-containing surfactants as wetters in SU-containing solid formulations results in a pronounced stabilization of the active ingredient in comparison with other wetters (e.g. ethoxylated fatty amines or alcohol ethoxylates). This effect can be observed mainly when water-soluble inorganic salts, such as ammonium sulfate or potassium sulfate, are present in addition to herbicidally active ingredients. The stabilizing effect is particularly pronounced when the wetter is employed at the concentration required for the biological action.

Storage-stable finished formulations with good biological activity can be obtained by mixing the SU with other active ingredients, sulfate- or sulfonate-containing surfactants and ammonium sulfate.

We have furthermore found processes for the preparation of the solid mixtures according to the invention and their use as crop protection compositions for controlling undesirable harmful plants.

Suitable sulfonylureas a) are generally compounds which have the structural unit

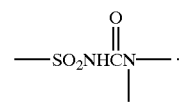

Preferred SU are those of the following structures I:

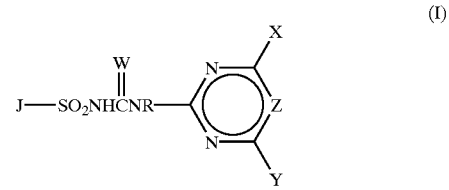

where J has the following meanings:

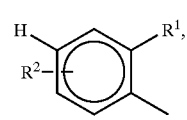

J-1

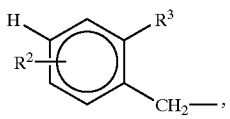

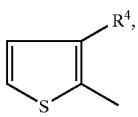

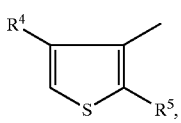

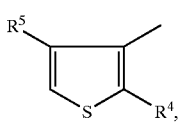

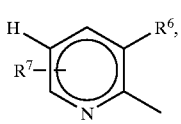

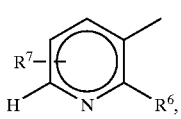

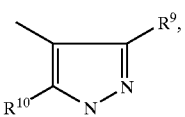

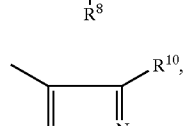

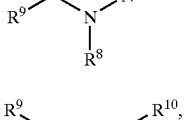

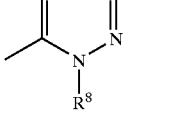

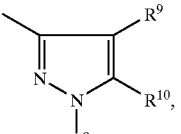

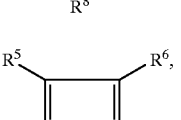

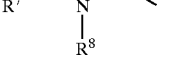

where the substituents R to $R^{18}$ have the following meanings:

R is H or $CH_3$;

$R^1$ is F, Cl, Br, $NO_2$, $C_1$–$C_4$-alkyl, $C_1$–$C_4$-haloalkyl, $C_3$–$C_4$-cycloalkyl, $C_2$–$C_4$-haloalkenyl, $C_1$–$C_4$-alkoxy, $C_1$–$C_4$-haloalkoxy, $C_2$–$C_4$-alkoxyalkoxy, $CO_2R^{12}$, $C(O)NR^{13}R^{14}$, $SO_2NR^{15}R^{16}$, $S(O)_nR^{17}$, $C(O)R^{18}$, $CH_2CN$ or L;

$R^2$ is H, F, Cl, Br, CN, $CH_3$, $OCH_3$, $SCH_3$, $CF_3$ or $OCF_2H$;

$R^3$ is Cl, $NO_2$, $CO_2CH_3$, $CO_2CH_2CH_3$, $SO_2N(CH_3)_2$, $SO_2CH_3$, $SO_2CH_2CH_3$, $OCH_3$ or $OCH_2CH_3$;

$R^4$ is $C_1$–$C_3$-alkyl, $C_1$–$C_4$-haloalkyl, $C_1$–$C_4$-alkoxy, $C_2$–$C_4$-haloalkenyl, F, Cl, Br, $NO_2$, $CO_2R^{12}$, $C(O)NR^{13}R^{14}$, $SO_2NR^{15}R^{16}$, $S(O)_nR^{17}$, $C(O)R^{18}$ or L;

$R^5$ is H, F, Cl, Br or $CH_3$;

$R^6$ is $C_1$–$C_4$-alkyl, $C_1$–$C_4$-alkoxy, $C_2$–$C_4$-haloalkenyl, F, Cl, Br, $CO_2R^{12}$, $C(O)NR^{13}R^{14}$, $SO_2NR^{15}R^{16}$, $S(O)_nR^{17}$, $C(O)R^{18}$ or L;

$R^7$ is H, F, Cl, $CH_3$ or $CF_3$;

$R^8$ is H, $C_1$–$C_4$-alkyl or pyridyl;

$R^9$ is $C_1$–$C_4$-alkyl, $C_1$–$C_4$-alkoxy, F, Cl, Br, $NO_2$, $CO_2R^{12}$, $SO_2NR^{15}R^{16}$, $S(O)_nR^{17}$, $OCF_2H$, $C(O)R^{18}$, $C_2$–$C_4$-haloalkenyl or L;

$R^{10}$ is H, Cl, F, Br, $C_1$–$C_4$-alkyl or $C_1$–$C_4$-alkoxy;

$R^{11}$ is H, $C_1$–$C_4$-alkyl, $C_1$–$C_4$-alkoxy, $C_2$–$C_4$-alkoxy, haloalkenyl, F, Cl, Br, $CO_2R^{12}$, $C(O)NR^{13}R^{14}$, $SO_2NR^{15}R^{16}$, $S(O)_nR^{17}$, $C(O)R^{18}$ or L;

$R^{12}$ is $C_1$–$C_4$-alkyl, unsubstituted or substituted by halogen, $C_1$–$C_4$-alkoxy or CN, allyl or propargyl;

$R^{13}$ is H, $C_1$–$C_4$-alkyl or $C_1$–$C_4$-alkoxy;

$R^{14}$ is $C_1$–$C_4$-alkyl;

$R^{15}$ is H, $C_1$–$C_4$-alkyl, $C_1$–$C_4$-alkoxy, allyl or cyclopropyl;

$R^{16}$ is H or $C_1$–$C_4$-alkyl;

$R^{17}$ is $C_1$–$C_4$-alkyl, $C_1$–$C_4$-haloalkyl, allyl or propargyl;

$R^{18}$ is $C_1$–$C_4$-alkyl, $C_1$–$C_4$-haloalkyl or $C_3$–$C_5$-cycloalkyl, unsubstituted or substituted by halogen;

is 0, 1 or 2;

L has the structure II

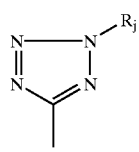

where
$R_j$ is H or $C_1$–$C_3$-alkyl;
W is O or S;
X is H, $C_1$–$C_4$-alkyl, $C_1$–$C_4$-alkoxy, $C_1$–$C_4$-haloalkoxy, $C_1$–$C_4$-haloalkyl, $C_1$–$C_4$-haloalkylthio, $C_1$–$C_4$-alkylthio, halogen, $C_2$–$C_5$-alkoxyalkyl, $C_2$–$C_5$-alkoxyalkoxy, amino, $C_1$–$C_3$-alkylamino or di($C_1$–$C_3$-alkyl)amino;
Y is H, $C_1$–$C_4$-alkyl, $C_1$–$C_4$-alkoxy, $C_1$–$C_4$-haloalkoxy, $C_1$–$C_4$-alkylthio, $C_1$–$C_4$-haloalkylthio, $C_2$–$C_5$-alkoxyalkyl, $C_2$–$C_5$-alkoxyalkoxy, amino, $C_1$–$C_3$-alkylamino, di($C_1$–$C_3$-alkyl)amino, $C_3$–$C_4$-alkenyloxy, $C_3$–$C_4$-alkanyloxy, $C_2$–$C_5$-alkylthioalkyl, $C_2$–$C_5$-alkylsulfinylalkyl, $C_2$–$C_5$-alkylsulfonylalkyl, $C_1$–$C_4$-haloalkyl, $C_2$–$C_4$-alkenyl, $C_3$–$C_5$-cycloalkyl, azido, fluorine or cyano;
Z is CH or N,
and the agriculturally useful salts thereof.

Some suitable SU together with their INN (International Nonproprietary Name) in accordance with Pesticide Manual may be mentioned below:

ACC 322140;
amidosulfuron;
azimsulfuron (N-[[(4,6-dimethoxy-2-pyrimidinyl)amino]-carbonyl]-1-methyl-4-(2-methyl-2H-tetrazol-5-yl)-1H-pyrazole-5-sulfonamide);
bensulfuron-methyl (methyl 2-[[[[(4,6-dimethoxy-2-pyrimidinyl)-amino]-carbonyl]amino]sulfonyl]methyl]benzoate);
ethyl 2-[[[[(4-chloro-6-methoxy-2-pyrimidinyl)-amino]carbonyl]amino]sulfonyl]benzoate(chlorimuron-ethyl);
2-chloro-N-[[(4-methoxy-6-methyl-1,3,5-triazin-2-yl)amino]-carbonyl]benzenesulfonamide(chlorosulfuron);
chlorosulfoxim;
cinosulfuron;
cyclosulfamuron;
ethametsulfuron-methyl (methyl 2-[[[[4-ethoxy-6-(methylamino)-1,3,5-triazin-2-yl]amino]carbonyl]amino]sulfonyl]benzoate);
ethoxysulfuron;
fluazasulfuron;
flupyrsulfuron (methyl 2-[[[[(4,6-dimethoxy-2-pyrimidinyl)-amino]carbonyl]amino]sulfonyl]-6-(trifluoromethyl)-3-pyridinecarboxylate);
halosulfuron-methyl
imazosulfuron;
methyl 2-[[[[(4-methoxy-6-methyl-1,3,5-triazin-2-yl)amino]-carbonyl]amino]sulfonyl]benzoate(metsulfuron-methyl);
nicosulfuron (2-[[[[(4,6-dimethoxy-2-pyrimidinyl)amino]-carbonyl]amino]sulfonyl]-N,N-dimethyl-3-pyridinecarboxamide); oxasulfuron;
primisulfuron (methyl 2-[[[[[4,6-bis(difluoromethoxy)-2-pyrimidinyl]amino]carbonyl]amino]sulfonyl]benzoate);
prosulfuron;
pyrazosulfuron-ethyl (ethyl 5-[[[[(4,6-dimethoxy-2-pyrimidinyl)-amino]carbonyl]amino]sulfonyl]-1-methyl-1H-pyrazole-4-carboxylate);
rimsulfuron (N-[[(4,6-dimethoxy-2-pyrimidinylamino]carbonyl]-3-(ethylsulfonyl)-2-pyridinesulfonamide); sulfosulfuron;
sulfometuron-methyl (methyl 2-[[[[(4,6-dimethyl-2-pyrimidinyl)-amino]carbonyl]amino]sulfonyl]benzoate);
thifensulfuron-methyl (methyl-3-[[[[(4-methoxy-6-methyl-1,3,5-triazin-2-yl)amino]carbonyl]amino]sulfonyl]-2-thiophene-carboxylate);
2-(2-chloroethoxy)-N-[[(4-methoxy-6-methyl-1,3,5-triazin-2-yl)-amino]carbonyl]benzenesulfonamide (triasulfuron);
tribenuron-methyl (methyl 2-[[[[N-(4-methoxy-6-methyl-1,3,5-triazin-2-yl)-N-methylamino]carbonyl]amino]sulfonyl]benzoate); and
triflusulfuron-methyl (Methyl 2-[[[[[4-(dimethylamino)-6-(2,2,2-trifluoroethoxy)-1,3,5-triazin-2-yl]amino]carbonyl]-amino]sulfonyl]-3-methylbenzoate).

Especially preferred are sulfonylureas of the formula III (which corresponds to the formula I where $J=J_1$), as are disclosed in, for example, EP-A 388 873, EP-A 559 814, EP-A 291 851 and EP-A 446 743:

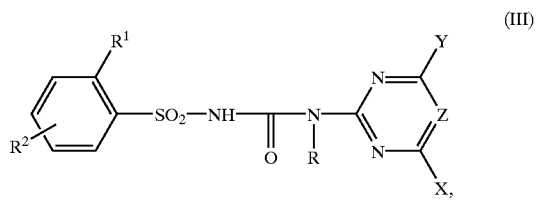

where the substituents have the following meanings:
$R^1$ is $C_1$–$C_4$-alkyl which can have attached to it one to five of the following groups: methoxy, ethoxy, $SO_2CH_3$, cyano, chlorine, fluorine, $SCH_3$, $S(O)CH_3$;
halogen;
a group $ER^{19}$ where E is O, S or $NR^{20}$;
$COOR^{12}$;
$NO_2$;
$S(O)_n R^{17}$, $SO_2 NR^{15}R^{16}$, $CONR^{13}R^{14}$;
$R^2$ is hydrogen, methyl, halogen, methoxy, nitro, cyano, trifluoromethyl, trifluoromethoxy, difluoromethoxy or methylthio,
Y is F, $CF_3$, $CF_2Cl$, $CF_2H$, $OCF_3$, $OCF_2Cl$, $C_1$–$C_4$-alkyl or $C_1$–$C_4$-alkoxy;
X is $C_1$–$C_2$-alkoxy, $C_1$–$C_2$-alkyl, $C_1$–$C_2$-alkylthio, $C_1$–$C_2$-alkylamino, di-$C_1$–$C_2$-alkylamino, halogen, $C_1$–$C_2$-haloalkyl, $C_1$–$C_2$-haloalkoxy,
R is hydrogen or methyl;
$R^{19}$ is $C_1$–$C_4$-alkyl, $C_2$–$C_4$-alkenyl, $C_2$–$C_4$-alkynyl or $C_3$–$C_6$-cycloalkyl, which can have attached to them 1 to 5 halogen atoms; furthermore in the event that E is O or $NR^{20}$, $R^{19}$ is also methylsulfonyl, ethylsulfonyl, trifluoromethylsulfonyl, allylsulfonyl, propargylsulfonyl or dimethylsulfamoyl;
$R^{20}$ is hydrogen, methyl or ethyl;
$R^{12}$ is a $C_1$–$C_4$-alkyl group, which can have attached to it up to three of the following radicals: halogen, $C_1$–$C_4$-alkoxy, allyl or propargyl;
$R^{17}$ is a $C_1$–$C_4$-alkyl group, which can have attached to it one to three of the following radicals: halogen, $C_1$–$C_4$-alkoxy, allyl or propargyl;
$R^{15}$ is hydrogen, a $C_1$–$C_2$-alkoxy group or a $C_1$–$C_4$-alkyl group;
$R^{16}$ is hydrogen or a $C_1$–$C_4$-alkyl group;

n is 1 or 2 and

Z is N or CH.

Particularly preferred sulfonylureas of the formula III are those of the formula I where J is $J_1$ and the rest of the substituents have the following meanings:

$R^1$ is $CO_2CH_3$, $CO_2C_2H_5$, $CO_2iC_3H_7$, $CF_3$, $CF_2H$, $OSO_2CH_3$, $OSO_2N(CH_3)_2$, Cl, $NO_2$, $SO_2N(CH_3)_2$, $SO_2CH_3$ or $N(CH_3)SO_2CH_3$, $R^2$ is hydrogen, Cl, F or $C_1$–$C_2$-alkyl, Y is $CF_2H$, $OCF_3$, $OCF_2Cl$, $CF_2Cl$, $CF_3$ or F, X is $OCH_3$, $OC_2H_5$, $OCF_3$, $OCF_2Cl$, $CF_3$, Cl, F, $NH(CH_3)$, $N(CH_3)_2$ or $C_1$–$C_2$-alkyl, $R^5$ is hydrogen and Z is N or CH.

Very especially preferred compounds of the formula III are compiled in the table which follows.

TABLE

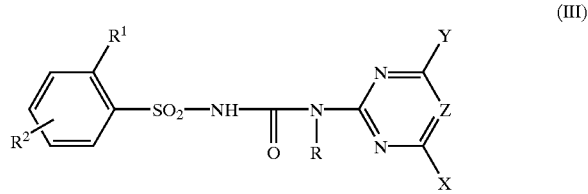

(III)

| No. | $R^1$ | $R^2$ | R | Y | X | Z |
|---|---|---|---|---|---|---|
| 1 | $CO_2CH_3$ | H | H | $OCF_2Cl$ | $OCH_3$ | CH |
| 2 | $CO_2C_2H_5$ | H | H | $OCF_2Cl$ | $OCH_3$ | CH |
| 3 | $CO_2iC_3H_7$ | H | H | $OCF_2Cl$ | $OCH_3$ | CH |
| 4 | $NO_2$ | H | H | $OCF_2Cl$ | $OCH_3$ | CH |
| 5 | $SO_2CH_3$ | H | H | $OCF_2Cl$ | $OCH_3$ | CH |
| 6 | $SO_2N(CH_3)_2$ | H | H | $OCF_2Cl$ | $OCH_3$ | CH |
| 7 | Cl | H | H | $OCF_2Cl$ | $OCH_3$ | CH |
| 8 | $N(CH_3)SO_2CH_3$ | H | H | $OCF_2Cl$ | $OCH_3$ | CH |
| 9 | $OSO_2CH_3$ | H | H | $OCF_2Cl$ | $OCH_3$ | CH |
| 10 | $OSO_2N(CH_3)_2$ | H | H | $OCF_2Cl$ | $OCH_3$ | CH |
| 11 | $CF_3$ | H | H | $OCF_2Cl$ | $OCH_3$ | CH |
| 12 | $CF_2H$ | H | H | $OCF_2Cl$ | $OCH_3$ | CH |
| 13 | $CO_2CH_3$ | H | H | $OCF_3$ | $OCH_3$ | CH |
| 14 | $CO_2C_2H_5$ | H | H | $OCF_3$ | $OCH_3$ | CH |
| 15 | $CO_2iC_3H_7$ | H | H | $OCF_3$ | $OCH_3$ | CH |
| 16 | $NO_2$ | H | H | $OCF_3$ | $OCH_3$ | CH |
| 17 | $SO_2CH_3$ | H | H | $OCF_3$ | $OCH_3$ | CH |
| 18 | $SO_2N(CH_3)_2$ | H | H | $OCF_3$ | $OCH_3$ | CH |
| 19 | Cl | H | H | $OCF_3$ | $OCH_3$ | CH |
| 20 | $N(CH_3)SO_2CH_3$ | H | H | $OCF_3$ | $OCH_3$ | CH |
| 21 | $OSO_2CH_3$ | H | H | $OCF_3$ | $OCH_3$ | CH |
| 22 | $OSO_2N(CH_3)_2$ | H | H | $OCF_3$ | $OCH_3$ | CH |
| 23 | $CF_3$ | H | H | $OCF_3$ | $OCH_3$ | CH |
| 24 | $CF_2H$ | H | H | $OCF_3$ | $OCH_3$ | CH |
| 25 | $CO_2CH_3$ | H | H | F | $OCH_3$ | CH |
| 26 | $CO_2C_2H_5$ | H | H | F | $OCH_3$ | CH |
| 27 | $CO_2iC_3H_7$ | H | H | F | $OCH_3$ | CH |
| 28 | $NO_2$ | H | H | F | $OCH_3$ | CH |
| 29 | $SO_2CH_3$ | H | H | F | $OCH_3$ | CH |
| 30 | $SO_2N(CH_3)_2$ | H | H | F | $OCH_3$ | CH |
| 31 | Cl | H | H | F | $OCH_3$ | CH |
| 32 | $N(CH_3)SO_2CH_3$ | H | H | F | $OCH_3$ | CH |
| 33 | $OSO_2CH_3$ | H | H | F | $OCH_3$ | CH |
| 34 | $OSO_2N(CH_3)_2$ | H | H | F | $OCH_3$ | CH |
| 35 | $CF_3$ | H | H | F | $OCH_3$ | CH |
| 36 | $CF_2H$ | H | H | F | $OCH_3$ | CH |
| 37 | $CO_2CH_3$ | H | H | $CF_3$ | $OCH_3$ | N |
| 38 | $CO_2C_2H_5$ | H | H | $CF_3$ | $OCH_3$ | N |
| 39 | $CO_2iC_3H_7$ | H | H | $CF_3$ | $OCH_3$ | N |
| 40 | $NO_2$ | H | H | $CF_3$ | $OCH_3$ | N |
| 41 | $SO_2CH_3$ | H | H | $CF_3$ | $OCH_3$ | N |
| 42 | $SO_2N(CH_3)_2$ | H | H | $CF_3$ | $OCH_3$ | N |
| 43 | Cl | H | H | $CF_3$ | $OCH_3$ | N |
| 44 | $N(CH_3)SO_2CH_3$ | H | H | $CF_3$ | $OCH_3$ | N |
| 45 | $OSO_2CH_3$ | H | H | $CF_3$ | $OCH_3$ | N |

TABLE-continued

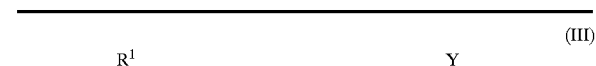

(III)

| No. | $R^1$ | $R^2$ | R | Y | X | Z |
|---|---|---|---|---|---|---|
| 46 | $OSO_2N(CH_3)_2$ | H | H | $CF_3$ | $OCH_3$ | N |
| 47 | $CF_3$ | H | H | $CF_3$ | $OCH_3$ | N |
| 48 | $CF_2H$ | H | H | $CF_3$ | $OCH_3$ | N |
| 49 | $CO_2CH_3$ | H | H | $CF_3$ | $OCH_3$ | CH |
| 50 | $CO_2C_2H_5$ | H | H | $CF_3$ | $OCH_3$ | CH |
| 51 | $CO_2iC_3H_7$ | H | H | $CF_3$ | $OCH_3$ | CH |
| 52 | $NO_2$ | H | H | $CF_3$ | $OCH_3$ | CH |
| 53 | $SO_2CH_3$ | H | H | $CF_3$ | $OCH_3$ | CH |
| 54 | $SO_2N(CH_3)_2$ | H | H | $CF_3$ | $OCH_3$ | CH |
| 55 | Cl | H | H | $CF_3$ | $OCH_3$ | CH |
| 56 | $N(CH_3)SO_2CH_3$ | H | H | $CF_3$ | $OCH_3$ | CH |
| 57 | $OSO_2CH_3$ | H | H | $CF_3$ | $OCH_3$ | CH |
| 58 | $OSO_2N(CH_3)_2$ | H | H | $CF_3$ | $OCH_3$ | CH |
| 59 | $CF_3$ | H | H | $CF_3$ | $OCH_3$ | CH |
| 60 | $CF_2H$ | H | H | $CF_3$ | $OCH_3$ | CH |
| 61 | $CO_2CH_3$ | H | H | $CF_2H$ | $OCH_3$ | N |
| 62 | $CO_2C_2H_5$ | H | H | $CF_2H$ | $OCH_3$ | N |
| 63 | $CO_2iC_3H_7$ | H | H | $CF_2H$ | $OCH_3$ | N |
| 64 | $NO_2$ | H | H | $CF_2H$ | $OCH_3$ | N |
| 65 | $SO_2CH_3$ | H | H | $CF_2H$ | $OCH_3$ | N |
| 66 | $SO_2N(CH_3)_2$ | H | H | $CF_2H$ | $OCH_3$ | N |
| 67 | Cl | H | H | $CF_2H$ | $OCH_3$ | N |
| 68 | $N(CH_3)SO_2CH_3$ | H | H | $CF_2H$ | $OCH_3$ | N |
| 69 | $OSO_2CH_3$ | H | H | $CF_2H$ | $OCH_3$ | N |
| 70 | $OSO_2N(CH_3)_2$ | H | H | $CF_2H$ | $OCH_3$ | N |
| 71 | $CF_3$ | H | H | $CF_2H$ | $OCH_3$ | N |
| 72 | $CF_2H$ | H | H | $CF_2H$ | $OCH_3$ | N |
| 73 | $CO_2CH_3$ | H | H | $CF_2H$ | $OCH_3$ | CH |
| 74 | $CO_2C_2H_5$ | H | H | $CF_2H$ | $OCH_3$ | CH |
| 75 | $CO_2iC_3H_7$ | H | H | $CF_2H$ | $OCH_3$ | CH |
| 76 | $NO_2$ | H | H | $CF_2H$ | $OCH_3$ | CH |
| 77 | $SO_2CH_3$ | H | H | $CF_2H$ | $OCH_3$ | CH |
| 78 | $SO_2N(CH_3)_2$ | H | H | $CF_2H$ | $OCH_3$ | CH |
| 79 | Cl | H | H | $CF_2H$ | $OCH_3$ | CH |
| 80 | $N(CH_3)SO_2CH_3$ | H | H | $CF_2H$ | $OCH_3$ | CH |
| 81 | $OSO_2CH_3$ | H | H | $CF_2H$ | $OCH_3$ | CH |
| 82 | $OSO_2N(CH_3)_2$ | H | H | $CF_2H$ | $OCH_3$ | CH |
| 83 | $CF_3$ | H | H | $CF_2H$ | $OCH_3$ | CH |
| 84 | $CF_2H$ | H | H | $CF_2H$ | $OCH_3$ | CH |
| 85 | $CO_2CH_3$ | H | H | $CF_2Cl$ | $OCH_3$ | N |
| 86 | $CO_2C_2H_5$ | H | H | $CF_2Cl$ | $OCH_3$ | N |
| 87 | $CO_2iC_3H_7$ | H | H | $CF_2Cl$ | $OCH_3$ | N |
| 88 | $NO_2$ | H | H | $CF_2Cl$ | $OCH_3$ | N |
| 89 | $SO_2CH_3$ | H | H | $CF_2Cl$ | $OCH_3$ | N |
| 90 | $SO_2N(CH_3)_2$ | H | H | $CF_2Cl$ | $OCH_3$ | N |
| 91 | Cl | H | H | $CF_2Cl$ | $OCH_3$ | N |
| 92 | $N(CH_3)SO_2CH_3$ | H | H | $CF_2Cl$ | $OCH_3$ | N |
| 93 | $OSO_2CH_3$ | H | H | $CF_2Cl$ | $OCH_3$ | N |
| 94 | $OSO_2N(CH_3)_2$ | H | H | $CF_2Cl$ | $OCH_3$ | N |
| 95 | $CF_3$ | H | H | $CF_2Cl$ | $OCH_3$ | N |
| 96 | $CF_2H$ | H | H | $CF_2Cl$ | $OCH_3$ | N |
| 97 | $CO_2CH_3$ | 3-F | H | Cl | $OCH_3$ | CH |
| 98 | $CF_2CF_3$ | H | H | $CH_3$ | $OCH_3$ | N |
| 99 | $CF_2CF_3$ | H | H | $CH_3$ | $OCH_3$ | N |
| 100 | $SO_2C_2H_5$ | H | H | F | $OCH_3$ | CH |

Naturally, it is also possible to employ mixtures of a number of sulfonylureas as component a).

The solid formulations according to the invention comprise one or more sulfate- or sulfonate-containing surfactants as component b).

Suitable products are described, for example, in McCutheon's Emulsifiers and Detergents, Volume 1 1994, North American Edition, McCutheson Division, Glen Rock, N.J., USA, or in Volume 2 of this publication (International Edition). "Surfactants in Europe", A Directory of surface active agents available in Europe, 2nd edition, 1989, Terg Data, Darlington, England may also be mentioned.

Substances which may be mentioned by way of example are alkyl sulfates (Texapon®), alkylsulfonates (Lutensit®A-PS, Hostapur® SAS, Witconate® NAS, Texapon®SCO) alkylbenzenesulfonates (Lutensit® ALB-N-BASF, Rhodacal®-American Cyanamid), alpha-olefinsulfonates (Witconates® AOS, Hostapur® OSB), alkyl polyglycol ether sulfonates, alkyl ether sulfates (Witcolate®, Lutensits® A-ES) alkyl polyglycol ether sulfates, polyoxyalkylene alkylaryl ether sulfates, polyoxyalkylene styryl ether sulfates and dialkyl sulfosuccinates (Lutensit® ABO-BASF, Aerosol® OT-American Cyanamid, Emcol® -Witco, Geropon® -Rhone Poulenc) the sodium, potassium and ammonium salts thereof, or mixtures of these.

Especially preferred are alkylsulfonates, paraffinsulfonates and olefinsulfonates, which have attached to them a $C_8$–$C_{25}$-, preferably a $C_{10}$–$C_{20}$-, alkyl radical. Suitable products are commercially available under the names Lutensit® A-PS (BASF AG), Hostapur® SAS 60, Hostapur® OS (both by Hoechst AG), Witconate® NAS 8, Witconate® AOS, Witconate® 3203, Witconate® 1840-X (all by Witco Corporation) or Texapon® SCO (Henkel KGaA).

Component a) generally amounts to from 0.5 to 75% by weight, preferably 1 to 25% by weight, in the solid mixtures according to the invention, based on the total weight of the formulation.

The sulfate- or sulfonate-containing surfactants (component b) generally amount to from 1 to 75, in particular 1 to 50 and especially preferably 5 to 25,% by weight, based on the total weight of the formulation.

In addition to components a) and b), the solid mixtures according to the invention may comprise other active ingredients which are miscible with sulfonylureas or act as synergists together with these. Suitable products are known to those skilled in the art and are described in the literature. The following groups of other active ingredients may be mentioned by way of example by their INN:

c1: 1,3,4-thiadiazoles: buthidazoles, cyprazoles;
c2: amides: allidochlor (CDAA), benzoylprop-ethyl, bromobutide, chlorothiamid, dimepiperate, dimethenamid, diphenamid, etobenzanid (benzchlomet), flamprop-methyl, fosamin, isoxaben, monalide, naptalame, pronamid (propyzamid), propanil;
c3: aminophosphoric acids: bilanafos (bialaphos), buminafos, glufosinate-ammonium, glyphosate, sulfosate;
c4: aminotriazoles: amitrol;
c5: anilides: anilofos, mefenacet, thiafluamide;
c6: aryloxyalkanoic acids: 2,4-D, 2,4-DB, clomeprop, dichlorprop, dichlorprop-P, (2,4-DP-P), fenoprop (2,4,5-TP), fluoroxypyr, MCPA, MCPB, mecoprop, mecoprop-P, napropamide, napropanilide, triclopyr;
c7: benzoic acids: chloramben, dicamba;
c8: benzothiadiazinones: bentazone;
c9: bleachers: clomazone (dimethazone), diflufenican, fluorochloridone, flupoxam, fluridone, pyrazolate, sulcotrione (chloro-mesulone) isoxaflutol, 2-(2'-chloro-3'-ethoxy-4'-ethylsulfonyl-benzoyl)-4-methylcyclohexane-1,3-dione;
c10: carbamates: asulam, barban, butylate, carbetamide, chlorbufam, chlorpropham, cycloate, desmedipham, di-allate, EPTC, esprocarb, molinate, orbencarb, pebulate, phenisopham, phenmedipham, propham, prosulfocarb, pyributicarb, sulf-allate (CDEC), terbucarb, thiobencarb (benthiocarb), tiocarbazil, tri-allate, vernolate;
c11: quinolinecarboxylic acids: quinclorac, quinmerac;
c12: chloroacetanilides: acetochlor, alachlor, butachlor, butenachlor, diethatyl-ethyl, dimethachlor, dimethenamide (cf. also under category c2) metazachlor, metolachlor, pretilachlor, propachlor, prynachlor, terbuchlor, thenylchlor, xylachlor;
c13: cyclohexenones: alloxydim, caloxydim, clethodim, cloproxydim, cycloxydim, sethoxydim, tralkoxydim, 2-{1-[2-(4-chlorophenoxy)propyloxy-imino]butyl}-3-hydroxy-5-(2H-tetrahydrothiopyran-3-yl)-2-cyclo-hexen-1-one;
c14: dichloropropionic acids: dalapon;
c15: dihydrobenzofurans: ethofumesate;
c16: dihydrofuran-1-ones: flurtamone;
c17: dinitroanilines: benefin, butralin, dinitramin, ethalfluralin, fluchloralin, isopropalin, nitralin, oryzalin, pendimethalin, prodiamine, profluralin, trifluralin;
c18: dinitrophenols: bromofenoxim, dinoseb, dinoseb-acetate, dinoterb, DNOC;
c19: diphenyl ethers: acifluorfen-sodium, aclonifen, bifenox, chlornitrofen (CNP), difenoxuron, ethoxyfen, fluorodifen, fluoroglycofen-ethyl, fomesafen, furyloxyfen, lactofen, nitrofen, nitrofluorfen, oxyfluorfen;
c20: dipyridylenes: cyperquat, difenzoquat-methylsulfate, diquat, paraquat-dichloride;
c21: ureas: benzthiazuron, buturon, chlorbromuron, chloroxuron, chlortoluron, cumyluron, dibenzyluron, cycluron, dimefuron, diuron, dymron, ethidimuron, fenuron, fluormeturon, isoproturon, isouron, karbutilat, linuron, methabenzthiazuron, metobenzuron, metoxuron, monolinuron, monuron, neburon, siduron, tebuthiuron, trimeturon;
c22: imidazoles: isocarbamide;
c23: imidazolinones: imazamethapyr, imazapyr, imazaquin, imazethabenz-methyl (imazame),imazethapyr, imazamox;
c24: oxadiazoles: methazole, oxadiargyl, oxadiazone;
c25: oxiranes: tridiphane;
c26: phenols: bromoxynil, ioxynil;
c27: phenoxypropionic esters: clodinafop, cyhalofop-butyl, diclofop-methyl, fenoxaprop-ethyl, fenoxaprop-p-ethyl, fenthiaprop-ethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, guizalofop-p-ethyl, quizalofop-tefuryl;
c28: phenylacetic acids: chlorfenac (fenac);
c29: phenylpropionic acids: chlorophenprop-methyl;
c30: protoporphyrinogen IX oxydase inhibitors: benzofenap, cinidon-ethyl, flumiclorac-pentyl, flumioxazin, flumipropyn, flupropacil, fluthiacet-methyl, pyrazoxyfen, sulfentrazone, thidiazimine, carfentrazone, azafenidin;
c31: pyrazoles: nipyraclofen;
c32: pyridazines: chloridazon, maleic hydrazide, norflurazon, pyridate;
c33: pyridinecarboxylic acids: clopyralid, dithiopyr, picloram, thiazopyr;
c34: pyrimidyl ethers: pyrithiobac-acid, pyrithiobac-sodium, pyriminobac-methyl, bispyribenzoxim, bispyribac-sodium;
c35: sulfonamides: flumetsulam, metosulam, cloransulam-methyl, diclosulam;
c36: triazines: ametryn, atrazine, aziprotryn, cyanazine, cyprazine, desmetryn, dimethamethryn, dipropetryn, eglinazine-ethyl, hexazinon, procyazine, prometon, prometryn, propazin, secbumeton, simazine, simetryn, terbumeton, terbutryn, terbuthylazine, trietazine, dimesyflam;

c37: triazinones: ethiozin, metamitron, metribuzin;
c38: triazolecarboxamides: triazofenamid;
c39: uracils: bromacil, lenacil, terbacil;
c40: various: benazolin, benfuresate, bensulide, benzofluor, butamifos, cafenstrole, chlorthal-dimethyl (DCPA), cinmethylin, dichlobenil, endothal, fluorbentranil, mefluidide, perfluidone, piperophos, diflufenzopyr, diflufenzopyr-sodium or the environmentally compatible salts of the abovementioned groups of active ingredients.

Examples of other preferred active ingredients c) are bromobutide, dimethenamide, isoxaben, propanil, glufosinate-ammonium, glyphosate, sulfosate, mefenacet, thiafluamide, 2,4-D, 2,4-DB, dichlorprop, dichlorprop-P, dichlorprop-P(2,4-DP-P), fluoroxopyr, MCPA, mecoprop, mecoprop-P, dicamba, bentazone, clomazone, diflufenican, sulcotrione, isoxaflutole, phenmedipham, thiobencarb, quinclorac, quinmerac, acetochlor, alachlor, butachlor, metazachlor, metolachlor, pretilachlor, butroxydim, caloxydim, clethodim, cycloxydim, sethoxydim, tralkoxydim, 2-{1-[2-(4-chlorophenoxy)propyloxyimino]-butyl}-3-hydroxy-5-(2H-tetrahydrothiopyran-3-yl)-2-cyclohexen-1-one, pendimethalin, acifluorfen-sodium, bifenox, fluoroglycofen-ethyl, fomesafen, lactofen, chlortoluron, cycluron, dymron, isoproturon, methabenzthiazuron, imazaquin, imazamox, imazethabenz-methyl, imazethapyr, bromoxynil, ioxynil, clodinafop, cyhlaofop-butyl, fenoxyprop-ethyl, fenoxaprop-p-ethyl, haloxyfop-p-methyl, cinidon-ethyl, flumiclorac-pentyl, carfentrazone, flumipropyn, fluthiacet-methyl, pyridate, clopyralid, bispyribac-sodium, pyriminobac-methyl, flumetsulam, metosulam, atrazine, cyanazine, terbutylazine, benazolin, benfuresate, cafenstrole, cinemthylin, ammonium-bentazon, cloquintocet, diflufenzopyr, diflufenzopyr-sodium, pyraflufen-ethyl.

Particularly preferred are the following compounds c): 2,4-D, dichlorprop-P, MCPA, mecoprop-P, dicamba, bentazone, diflufenican, sulcotrione, quinclorac, caloxydim, cycloxydim, sethoxydim, 2-{1-[2-(4-chlorophenoxy)propyloxyimino]butyl}-3-hydroxy-5-(2H-tetrahydrothiopyran-3-yl)-2-cyclohexen-1-one, acifluorfen-sodium, fluoroglycofen-ethyl, bromoxynil, fenoxyprop-ethyl, cinidon-ethyl, atrazine, terbutylazine, ammonium-bentazone, cloquintocet, thiafluamid, isoxaflutole, diflufenzopyr, diflufenzopyr-sodium, carfentrazone, imazamox.

Very especially preferred are the following compounds c): 2,4-D, dichlorprop-P, mecoprop-P, MCPA, ammonium-bentazone, bentazone, diflufenican, quinclorac, 2-{1-[2-(4-chlorophenoxy)propyloxyimino]butyl}-3-hydroxy-5-(2H-tetrahydrothiopyran-3-yl)-2-cyclohexen-1-one, caloxydim, cycloxydim, sethoxydim, fluoroglycofen-ethyl, cinidon-ethyl, atrazine, terbutylazine, dicamba, diflufenzopyr and diflufenzopyr-sodium.

If any other active ingredients c) are present, they generally amount to from 0.5 to 75, preferably 1 to 60,% by weight of the formulation.

The solid mixtures according to the invention may additionally comprise formulation auxiliaries which are known per se in addition to the above-described components a), b) and c).

Suitable surfactants are the alkali metal salts, alkaline earth metal salts or ammonium salts of aromatic sulfonic acids, e.g. ligno-, phenol-, naphthalene- and dibutylnaphthalenesulfonic acid, and of fatty acids, alkyl polyglycosides, condensates of sulfonated naphthalene and its derivatives with formaldehyde, condensates of naphthalene or of the naphthalenesulfonic acids with phenol and formaldehyde, condensates of phenol or of phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated triarylphenols, salts of phosphated triarylphenol ethoxylates, polyoxypropylene alkyl ethers, lauryl alcohol polyglycol ether acetate, sorbitol esters, lignosulfite waste liquors or methylcellulose or mixtures of these.

When surface-active substances are used concomitantly, they generally amount to from 0.5 to 25% by weight, based on the total weight of the solid mixture.

The solid mixtures according to the invention can also be used together with carrier materials. Examples of carriers which may be mentioned are:

mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates or mixtures of these.

The following may be employed as other additives in amounts which are customary per se:

Water-soluble compounds or salts such as:
sodium sulfate, pottasium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate;

binders such as:
polyvinylpyrrolidone, polyvinyl alcohol, partially hydrolyzed polyvinyl acetate, carboxymethylcellulose, starch, vinylpyrrolidone/vinyl acetate copolymers and polyvinyl acetate or mixtures of these;

lubricants such as:
magenesium stearate, sodium stearate, talc or polyethylene glycol or mixtures of these;

antifoams such as:
silicone emulsions, long-chain alcohols, phosphoric esters, acetylene diols, fatty acids or organofluorine compounds, and complexing agents such as:
salts of ethylenediaminetetraacetic acid (EDTA), salts of trinitrilotriacetic acid or salts of polyphosphoric acids, or mixtures of these.

The solid mixtures according to the invention can be prepared in the form of powders, granules, briquettes, tablets and similar formulation variants. In addition to powders, granules are especially preferred. The powders may be water-soluble or water-dispersible powders. The granules may be water-soluble or water-dispersible granules for use in spray application, or so-called spreading granules for direct application. The mean particle size of the granules is generally between 200 $\mu$m and 2 mm.

The resulting granule formulations are dust-free, free-flowing products which do not cake and are readily soluble or dispersible in cold water.

Due to their characteristics, the products can be readily packaged in relatively large amounts. In addition to containers such as polymer, paper or laminated sacks or bags, the products can be handled in cardboard boxes or other containers. To avoid further exposure of the user, it is possible to package the products in water-soluble film bags, for example polyvinyl alcohol film bags, which are introduced directly into the spray tank, where they dissolve. Substances which can be employed for such water-soluble films are, inter alia, polyvinyl alcohol or cellulose derivatives such as methylcellulose, methylhydroxypropylcellulose or carboxymethylcellulose. Since the product is packaged in portions which are the right size for use, the user no longer comes into contact with it. The water-soluble bags are preferably packaged in an external sheath which is impermeable to water vapor, such as polyethylene film, polyethylene laminated paper or aluminum foil.

The solid formulations according to the invention can be prepared by various processes known to those skilled in the art.

A Preferred preparation processes for the abovementioned formulations which may be mentioned are extruder granulation, spray drying, fluidized-bed agglomeration, mixer granulation and disk granulation.

Fluidized-bed granulation (FBG) is especially suitable. Depending on the desired composition of the formulation, an aqueous solution, emulsion or suspension which comprises all product components is sprayed and agglomerated in an FBG apparatus.

However, it is also possible, if desired, to introduce active ingredient salts and/or inorganic ammonium salts into the apparatus and to spray them with a solution or emulsion/suspension of the remaining product constituents, during which process agglomerates are formed. It is furthermore possible to apply aqueous solutions, emulsions or suspensions which comprise specific product constituents to active ingredient granules, an active ingredient salt and/or an inorganic ammonium salt in succession, thus obtaining a variety of coating layers.

In general, the granules are dried sufficiently in the course of the fluidized-bed granulation process. However, it may be advantageous to produce a separate drying step after granulation, either in the same, or in a separate, dryer. After granulation/drying, the product is cooled and screened.

A further especially suitable process is extruder granulation. Suitable for extruder granulation are preferably basket, radial or dome extruders in which the granule kernel is subjected to a low degree of compaction.

To carry out the granulation, a mixture of solid substances is made into a paste with a granulation liquid in a suitable mixer until an extrudable mass is formed. This is extruded in one of the abovementioned extruders. To carry out the extrusion, apertures of dimensions between 0.3 and 3 mm are used (preferably 0.5–1.5 mm). Mixtures of solids which are used are mixtures of active ingredients, formulation auxiliaries and, if appropriate, water-soluble salts. These are generally pre-ground. In some cases, it suffices only to pre-grind, in suitable mills, those substances which are water-insoluble.

Suitable granulation liquids are water, the sulfate- or sulfonate-containing surfactants according to the invention or aqueous solutions of these. Also suitable are aqueous solutions of inorganic salts, non-ionic surfactants, anionic surfactants, solutions of binders such as polyvinylpyrrolidone, polyvinyl alcohol, carboxymethylcellulose, starch, vinylpyrrolidine/vinyl acetate copolymers, sugars, dextrin or polyethylene glycol. After extruder granulation, the resulting granules are dried and, if appropriate, screened in order to remove coarse particles and fines.

Comparison Example 1

A premix composed of:

| | |
|---|---|
| 73.1 g | of SU 1 (compound No. 47 of Table 1) (technical grade, 95.7%), |
| 8 g | of Tamol ® NH and |
| 17.9 g | of Ufoxane ® 3A | was mixed and ground in a high-speed rotor mill.

Also,

| | |
|---|---|
| 7.1 g | of premix, |
| 5 g | of Extrusil ® (Degussa) and |
| 77.9 g | of ammonium sulfate | were mixed with 24 g of Klearfac$^R$ AA-270 as a 50% aqueous solution in a Moulinette kitchen blender. The resulting mass was extruded by means of an extruder (KAR-75, Fitzpatrick Europe). The resulting moist granules were dried in a drying oven.

Comparison Example 2

A premix composed of:

| | |
|---|---|
| 73.1 g | of SU 1 (technical grade, 95.7%) |
| 8 g | of Tamol ® NH and |
| 17.9 g | of Ufoxane ® 3A | was mixed and ground in a high-speed rotor mill.

Also,

| | |
|---|---|
| 7.1 g | of premix, |
| 15 g | of Extrusil ® (Degussa) and |
| 77.9 g | of ammonium sulfate | were mixed with 23 g of Armoblem$^R$ 557 as a 50% aqueous solution in a Moulinette kitchen blender. The resulting mass was extruded by means of an extruder (KAR-75, Fitzpatrick Europe). The resulting moist granules were dried in a drying oven.

Comparison Example 3

A premix composed of:

| | |
|---|---|
| 73.1 g | of SU 1 (technical grade, 95.7%), |
| 8 g | of Tamol ® NH and |
| 17.9 g | of Ufoxane ® 3A | was mixed and ground in a high-speed rotor mill.

Also,

| | |
|---|---|
| 7.1 g | of premix, |
| 15 g | of Extrusil ® (Degussa) and |
| 77.9 g | of ammonium sulfate | were mixed with 29 g of Lutensol$^R$ ON 80 as a 50% aqueous solution in a Moulinette kitchen blender. The resulting mass was extruded by means of an extruder (KAR-75, Fitzpatrick Europe). The resulting moist granules were dried in a drying oven.

Comparison Example 4

A mixture composed of:

| | |
|---|---|
| 6.9 g | of metsulfuron-methyl (technical grade, 99%) |
| 3 g | of Tamol ® NH |
| 6 g | of Ufoxane ® 3A |
| 15 g | of Extrusil ® and |
| 43.1 g | of ammonium sulfate | was mixed thoroughly and ground by means of a laboratory high-speed rotor mill. The resulting powder mixture was mixed with 17 parts of Lutensol$^R$ ON 30 in a planetary paddle mixer (Kenwood Chef). The resulting mass was extruded by means of an extruder (DGL-1, Fitzpatrick Europe). The resulting moist granules were dried in a fluidized-bed dryer.

EXAMPLE 1

A premix composed of:

| | |
|---|---|
| 73.1 g | of SU 1 (technical grade, 95.7%) |
| 8 g | of Tamol ® NH and |
| 17.9 g | of Ufoxane ® 3A | was mixed and ground in a high-speed rotor mill.
Also,

| | |
|---|---|
| 7.1 g | of premix, |
| 5 g | of Tamol ® NH, |
| 58.9 g | of ammonium sulfate, |
| 3 g | of Sipernat ® 22, |
| 25 g | of Lutensit ® A-LBN and |
| 1 g | of antifoam emulsion SRE | were made into a paste with 14 ml of water in a Moulinette kitchen blender. The resulting mass was extruded by means of an extruder (KAR-75, Fitzpatrick Europe). The resulting moist granules were dried in a drying oven.

EXAMPLE 2

A premix composed of:

| | |
|---|---|
| 73.1 g | of SU 1, technical grade, |
| 17.9 g | of Ufoxane ® 3A and |
| 8 g | of Tamol ® NH | was mixed and ground in a high-speed rotor mill.

Also,

| | |
|---|---|
| 7.1 g | of premix, |
| 15 g | of Extrusil ®, |
| 52.9 g | of ammonium sulfate and |
| 25 g | of Lutensit ® A-PS | were made into a paste with 14 ml of water in a Moulinette kitchen blender. The resulting mass was extruded by means of an extruder (KAR-75, Fitzpatrick Europe). The resulting moist granules were dried in a drying oven.

EXAMPLE 3

A premix composed of:

| | |
|---|---|
| 73.1 g | of SU 1 (technical grade, 95.7%) |
| 8 g | of Tamol ® NH and |
| 17.9 g | of Ufoxane ® 3A | was mixed and ground in a high-speed rotor mill.
Also,

| | |
|---|---|
| 7.1 g | of premix, |
| 15 g | of Extrusil$^R$ (Degussa), |
| 52.9 g | of potassium sulfate and |
| 24 g | of Lutensit$^R$ AP-S | were mixed in a Moulinette kitchen blender. The resulting mass was extruded by means of an extruder (KAR-75, Fitzpatrick Europe). The resulting moist granules were dried in a drying oven.

EXAMPLE 4

A mixture composed of:

| | |
|---|---|
| 5.1 g | of SU 1 (technical grade, 98.54%) |
| 3 g | of Tamol$^R$ NH |
| 6 g | of Ufoxane$^R$ 3A |
| 15 g | of Extrusil$^R$ (Degussa) and |
| 44.9 g | of ammonium sulfate | was mixed and ground in a high-speed rotor mill.

In a Moulinette kitchen blender, the resulting powder was mixed with 25 g of Witconate$^R$ 3203 and 1 g of antifoam SRE. The resulting mass was extruded by means of an extruder (KAR-75, Fitzpatrick Europe). The resulting moist granules were dried in a drying oven.

EXAMPLE 5

A mixture composed of:

| | |
|---|---|
| 5.1 g | of SU 1 (technical grade, 98.54%) |
| 3 g | of Tamol$^R$ NH |
| 6 g | of Ufoxane$^R$ 3A |
| 15 g | of Extrusil$^R$ (Degussa) and |
| 44.9 g | of ammonium sulfate | was mixed and ground in a high-speed rotor mill. In a Moulinette kitchen blender, the resulting powder was mixed with 25 g of Witconate$^R$ NAS 8 and 1 g of antifoam SRE. The resulting mass was extruded by means of an extruder (KAR-75, Fitzpatrick Europe). The resulting moist granules were dried in a drying oven.

EXAMPLE 6

A premix composed of:

| | |
|---|---|
| 5.1 g | of SU 1 (technical grade, 98.5%) |
| 3.1 g | of cinidon-ethyl (technical grade, 98%) |
| 1 g | of Tamol$^R$ NH |
| 2 g | of Ufoxane$^R$ 3A |
| 15 g | of Extrusil$^R$ (Degussa) and |
| 47.8 g | of ammonium sulfate | was mixed and ground in a jet mill.

Also,

| | |
|---|---|
| 74 g | of premix, |
| 25 g | of Lutensit$^R$ APS (alkylsulfonate, BASF AG, technical grade, 65%) and |
| 1 g | of antifoam SRE | were mixed in a planetary paddle mixer (Kenwood Chef), and a total of 6.5 g of water (based on 100 g of product) was added. The resulting mass was extruded by means of an extruder (DGL-1, Fitzpatrick Europe). The resulting moist granules were dried in a fluidized-bed dryer. This gave readily dispersible granules.

EXAMPLE 7

A premix composed of:

| | |
|---|---|
| 5.1 g | of SU 1 (technical grade, 98.5%) |
| 3.1 g | of cinidon-ethyl (technical grade, 98%) |
| 1 g | of Tamol$^R$ NH |
| 2 g | of Ufoxane$^R$ 3A |
| 15 g | of Extrusil$^R$ (Degussa) and |
| 47.8 g | of ammonium sulfate | was mixed and ground in a jet mill.

Also,

| | |
|---|---|
| 74 g | of premix, |
| 22.5 g | of Lutensit$^R$ APS (alkylsulfonate, BASF AG, technical grade, 65%) and |
| 1 g | of antifoam SRE | were mixed in a planetary paddle mixer (Kenwood Chef), and a total of 5 g of water (based on 100 g of product) was added. The resulting mass was extruded by means of an extruder (DGL-1, Fitzpatrick Europe). The resulting moist granules were dried in a fluidized-bed dryer. This gave readily dispersible granules.

EXAMPLE 8

A premix composed of:

| | |
|---|---|
| 6 g | of SU 1 |
| 10 g | of clefoxydim-lithium |
| 10 g | of Extrusil$^R$ |
| 10 g | of urea |
| 3 g | of Morwet$^R$ EFW |
| 1 g | of Aerosol$^R$ TO B and |
| 40 g | of Tamol$^R$ NH | was mixed thoroughly and ground by means of an air-jet mill. The resulting powder mixture was mixed with 20 parts of Lutensit$^R$ APS in a planetary paddle mixer (Kenwood Chef). To produce an extrudable mass, 1.8% of water was also added. The resulting mass was extruded by means of an extruder (DGL-1, Fitzpatrick Europe). The resulting moist granules were dried in a fluidized-bed dryer.

EXAMPLE 9

A mixture composed of:

| | |
|---|---|
| 6.9 g | of metsulfuron-methyl (technical grade, 99%) |
| 3 g | of Tamol$^R$ NH, |
| 6 g | of Ufoxane$^R$ 3A, |
| 15 g | of Extrusil$^R$ and |
| 43.1 g | of ammonium sulfate | was mixed thoroughly and ground by means of a laboratory high-speed rotor mill. The resulting powder mixture was mixed with 25 parts of Lutensit$^R$ APS in a planetary paddle mixer (Kenwood Chef). The resulting mass was extruded by means of an extruder (DGL-1, Fitzpatrick Europe). The resulting moist granules were dried in a fluidized-bed dryer.

The table which follows illustrates the components employed in the examples:

TABLE 2

| Name | Chemical name | Manufacturer |
|---|---|---|
| Tamol ® NH | Naphthalenesulfonic acid/formaldehyde condensate | BASF AG |
| Ufoxane ® 3A | Sodium ligno-sulfonate | Borregaard |
| Morwet ® D425 | Naphthalenesulfonic acid/formaldehyde condensate | BASF AG |
| Wettol ® NT 1 | Alkylnaphthalene-sulfonate | BASF AG |
| Extrusil ® | Highly disperse calcium silicate | Degussa |
| Sipernat ® 22 | Highly disperse silica | Degussa |
| Antischaummittel SRE | Silicone oil emulsion | Wacker-Chemie |
| Lutensol ® ON 30 | Fatty alcohol ethoxylate (3EO) | BASF AG |
| Lutensol ® ON 60 | Fatty alcohol ethoxylate (6EO) | BASF AG |
| Lutensol ® ON 80 | Fatty alcohol ethoxylate (8EO) | BASF AG |
| Lutensit ® A-PS | Sodium alkane-sulfonate | BASF AG |
| Lutensit ® A-LBN | Sodium alkylbenzene-sulfonate | BASF AG |
| Armoblem ® 557 | Ethoxylated fatty amine | Akzo |

TABLE 2-continued

| Name | Chemical name | Manufacturer |
|---|---|---|
| Klearfac ® AA-270 | Phosphated fatty alcohol ethoxylate | BASF Corporation |
| Morwet ® EFW | Anionic wetter blend | Witco |
| Witconate 3203 | Sodium alpha-olefin-sulfonate | Witco |
| Witconate NAS 8 | Sodium alkane-sulfonate | Witco |
| Aerosol OT-B | Sodium dioctylsulfo-succinate | American Cyanamid |
| SU 1 | Comp. 47 of Table 1 | |
| Clefoxydim | 2-{1-[2-(4-chloro-phenoxy)propyloxyamino]butyl}-5-tetrahydrothiopyran-3-yl-cyclohexane-1,3-dione | |
| Cinidon-ethyl | ethyl (Z)-2-chloro-3-[2-chloro-5-(4,5,6,7-tetrahydro-1,3-dioxoisoindoledion-2-yl)-phenyl]acrylate | |

Test Methods

The active ingredient content of SU of the formulations given in the above examples was determined in each case by means of quantitative HPLC and is given in Table 3 in per cent.

Storage Stability Tests

To test for storage stability, samples of the formulation in question as described in Examples 1–9 and Comparison Examples 1 to 4 were stored for a specified time (14 days or 42 days) in tightly sealed glass containers at the temperature indicated (40° C., 50° C. or 54° C.). The samples are then examined and compared with the comparison value at the beginning of the storage period (zero value). The active ingredient content is given as relative SU content, based on the zero value (in per cent). The storage tests were carried out by a method similar to CIPAC MT 46. The long-term stability of a product is estimated on the basis of short-term storage at elevated temperature.

Table 3 shows the results from the determination of the storage stability of the solid mixtures prepared as shown in Examples 1–9 and comparison Examples 1–4.

The results demonstrate the superior characteristics of the solid mixtures according to the invention.

TABLE 3

| Ex. No. | Adjuvant | Active ingredient content, in % by weight | Relative active ingredient content of SU after 14 days, 54° C. |
|---|---|---|---|
| C1 | Klearfac ® AA-270 | 4.3 | 0 |
| C2 | Armoblem ® 557 | 3.9 | 13 |
| C3 | Lutensit ® ON 60 | 3.2 | 14 |
| C4 | Lutensol ® ON 30 | 7.3 | 48 |
| 1 | Lutensit ® A-LBN | 5 | 90 |
| 2 | Lutensit ® A-PS | 5.1 | 88 |
| 3 | Lutensit ® A-PS | 5.5 | 100 |
| 4 | Witconate ® 3203 | 5.5 | 93 |
| 5 | Witconate ® NAS 8 | 5.6 | 90 |
| 6 | Lutensit ® A-PS | 5.38 | 95 |
| 7 | Lutensit ® A-PS | 5.57 | 94[1] |
| 8 | Lutensit ® A-PS | 6.4 | 100 |
| 9 | Lutensit ® A-PS | 7.3 | 69 |

[1] measured after storage for 30 days at 50° C.

We claim:

1. A solid mixture comprising
a) a sulfonylurea of the formula III

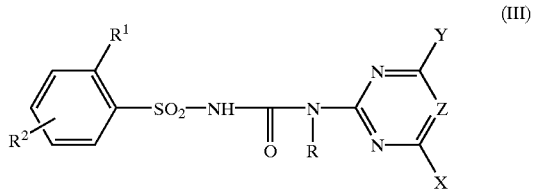

where the substituents have the following meanings:
$R^1$ is $C_1$–$C_4$-alkyl which can have attached to it one to five of the following groups: methoxy, ethoxy, $SO_2CH_3$, cyano, chlorine, fluorine, $SCH_3$, $S(O)CH_3$;
halogen;
a group $ER^{19}$ where E is O, S or $NR^{20}$;
$COOR^{12}$;
$NO_2$;
$S(O)_nR^{17}$, $SO_2NR^{15}R^{16}$, $CONR^{13}R^{14}$;
$R^2$ is hydrogen, methyl, halogen, methoxy, nitro, cyano, trifluoromethyl, trifluoromethoxy, difluoromethoxy or methylthio,
Y is F, $CF_3$, $CF_2Cl$, $CF_2H$, $OCF_3$, $OCF_2Cl$, $C_1$–$C_4$-alkyl or $C_1$–$C_4$-alkoxy;
X is $C_1$–$C_2$-alkoxy, $C_1$–$C_2$-alkyl, $C_1$–$C_2$-alkylthio, $C_1$–$C_2$-alkylamino, di-$C_1$–$C_2$-alkylamino, halogen, $C_1$–$C_2$-haloalkyl, $C_1$–$C_2$-haloalkoxy,
R is hydrogen or methyl;
$R^{19}$ is $C_1$–$C_4$-alkyl; $C_2$–$C_4$-alkenyl, $C_2$–$C_4$-alkynyl or $C_3$–$C_6$-cycloalkyl, which can have attached to them 1 to 5 halogen atoms; furthermore, in the event that E is O or $NR^{20}$, $R^{19}$ is also methylsulfonyl, ethylsulfonyl, trifluoromethylsulfonyl, allylsulfonyl, propargylsulfonyl or dimethylsulfamoyl;
$R^{20}$ is hydrogen, methyl or ethyl;
$R^{12}$ is a $C_1$–$C_4$-alkyl group, which can have attached to it up to three of the following radicals: halogen, $C_1$–$C_4$-alkoxy, allyl or propargyl;
$R^{17}$ is a $C_1$–$C_4$-alkyl group, which can have attached to it one to three of the following radicals: halogen, $C_1$–$C_4$-alkoxy, allyl or propargyl;
$R^{15}$ is hydrogen, a $C_1$–$C_2$-alkoxy group or a $C_1$–$C_4$-alkyl group;
$R^{16}$ is hydrogen or a $C_1$–$C_4$-alkyl group;
n is 1–2 and
Z is N or CH and
b) an alkyl sulfonate-containing surfactant.

2. A solid mixture as claimed in claim 1, comprising a further herbicidally active ingredient.

3. A solid mixture as claimed in claim 1, comprising 0.5 to 75% by weight of component a).

4. A solid mixture as claimed in claim 1, comprising 1 to 50% by weight of component b).

5. A method of controlling undesired vegetation, which comprises treating the plants and/or the area to be kept free of the plants with a herbicidally active amount of a solid mixture as claimed in claim 1.

6. A process for the preparation of herbicide formulations, which comprises mixing a sulfonylurea of the formula III with a sulfonate-containing surfactant to obtain a solid mixture as claimed in claim 1.

7. A solid mixture as claimed in claim 4, comprising 5 to 25% by weight of component b).

* * * * *